United States Patent [19]

Tsuchihashi et al.

[11] Patent Number: 4,604,486

[45] Date of Patent: Aug. 5, 1986

[54] METHOD OF PREPARING OPTICALLY ACTIVE KETONES

[75] Inventors: Genichi Tsuchihashi, Tama; Keisuke Suzuki, Chigasaki, both of Japan

[73] Assignee: Toyo Stauffer Chemical Co., Ltd., Tokyo, Japan

[21] Appl. No.: 689,007

[22] Filed: Jan. 4, 1985

[51] Int. Cl.$^4$ ............................................. C07C 45/51
[52] U.S. Cl. ................................. 568/322; 568/404
[58] Field of Search .............. 568/404, 405, 361, 322; 260/465 R

[56] References Cited

U.S. PATENT DOCUMENTS

| | | | |
|---|---|---|---|
| 2,042,224 | 5/1936 | Groll et al. | 568/405 |
| 3,235,602 | 2/1966 | Russell | 568/405 |
| 3,491,153 | 1/1970 | Lyness | 568/322 |
| 4,085,136 | 4/1978 | Tucker | 260/465 R |
| 4,128,584 | 12/1978 | Martel et al. | 260/465 R |

OTHER PUBLICATIONS

Suzuki et al, Tetrahedron Letters, vol. 25, pp. 1817–1820 (1984).
Suzuki et al, Tetrahedron Letters, vol. 24, pp. 4997–5000 (1983).
Ben M. Benjamin, Howard J. Schaeffer and Clair J. Collins, "The Deamination of 1,1-Diphenyl-2-Amino-1-Propanol", J. Am. Chem. Soc., 79, 6160 (1957).
R. G. Riley and R. M. Silverstein, "Synthesis of S-(+-)-4-Methyl-3-Heptanone, The Principal Alarm Pheromone of Atta Texana, and Its Enantiomer", *Tetrahedron* 30, pp. 1171–1174 (1974).
K. Mori, "Absolute Configuration of (−)-4-methyl-heptan-3-ol, A Pheromone of the Smaller European Elm Bark Beetle, as Determined by the Synthesis of Its (3R,4R)-(+)- and (3S,4R)-(+)-Isomers", *Tetrahedron*, 33 pp. 289–294 (1977).
Von Dieter Enders and Herbert Eichenauer, "Asymmetrische Synthesis von Ameisen-Alarmpheromonen-Alpha-Alkylierung von Acyclischen Ketonen Mit Praktisch Vollstandiger Asymmetrischer Induktion", *Angewandte Chemie* 91, 425 pp. 425–427 (1979).

Primary Examiner—James H. Reamer
Attorney, Agent, or Firm—Oblon, Fisher, Spivak, McClelland & Maier

[57] ABSTRACT

A method of preparing optically active ketones having the general formula

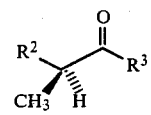

wherein $R^2$ and $R^3$ indicate hydrocarbon groups having 1 to 20 carbon atoms characterized by submitting an optically active sulfonyloxy alcohol having the general formula

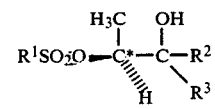

wherein $R^1$, $R^2$ and $R^3$ indicate hydrocarbon groups having carbon atoms of 1 to 20 and which optionally contain N, O, P and S. The symbol * indicates asymmetric carbon atoms to rearrangement in a solvent and in the presence of organoaluminum compounds given by the general formula $R_{3-n}^4 AlX_n$, (wherein $R^4$ indicates an alkyl group having carbon atoms of 1 to 20 and X indicates a halogen atom, an alkoxy group or a CN group. n is 1, 1.5 or 2).

7 Claims, No Drawings

METHOD OF PREPARING OPTICALLY ACTIVE KETONES

DETAILED DESCRIPTION OF THE INVENTION

The present invention relates to a novel method of preparing optically active ketones. In more detail, the invention relates to a novel method of preparing optically active ketones having the general formula

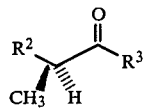

(wherein $R^2$ and $R^3$ indicate hydrocarbon groups having carbon atoms of 1 to 20.) characterized by submitting an optically active sulfonyloxy alcohol having the general formula:

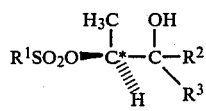

(wherein $R^1$, $R^2$ and $R^3$ indicate hydrocarbon groups having carbon atoms of 1 to 20 and which optionally contain N, O, P and S. * indicates asymmetric carbon atoms.) to pinacol rearrangement in the presence of organoaluminum compounds having the general formula $R^4{}_{3-n}AlX_n$ (wherein $R^4$ indicates an alkyl group having carbon atoms of 1 to 20 and X indicates a halogen atom, an alkoxy group or a CN group. n is 1, 1.5 or 2.).

Recently, an attempt to develop insect phermones as agricultural chemicals has been made actively. (S)-4-methyl-3-hexanone prepared in accordance with the invention is a substance used against the ant which is known as the alarm pheromone of the ant. When using this for the expulsion of the ant, there are few, if any, influences upon the human body and the environment, since this is a natural substance. Moreover, the insect has an ability to distinguish two enantiomers. Therefore, it is necessary to prepare the ketone enantio-selectively.

For the preparation of this optically active ketone which is the alarm pheromone, the resolution of a racemic modification has been necessary hitherto which is multistage and/or is time-consuming and uneconomical (*Tetrahedron* 30, 1174 (1974) and *Tetrahedron* 33, 289 (1977)).

For the purpose of improving the shortcoming described above, a method was proposed in *Angewandte Chemie* 91, 425 (1979), which would allow the preparation of the optically active ketone enantio-selectively. However, this method necessitates many kinds of reagents, and the final synthesis rate of the objective substance from starting material is low. Moreover, in this method, ketone is used as a starting material.

Further, no methods for preparing optically active ketones, in particular, acyclic ketones using alcohols as starting materials are known. Generally, when submitting alcohols to pinacol rearrangement, racemized ketones are obtained, even if optically active alcohols are used. For example, when treating (R)-2-amino-1,1-diphenyl-1-propanol with nitrous acid, (R)-1,2-diphenyl-1-propanone is obtained at 24% racemization rate (*J.Am. Chem. Soc.*, 79, 6160 (1957)).

In view of the situation described above, the inventors studied diligently on the method for preparing ketones easily and enantio-selectively using alcohols as starting materials and have invented a synthetic method of preparing optical active ketones previously through stereospecific 1,2 rearrangement using particularly triethylaluminum as a reaction promoter (Japanese Patent Application No. 195487/1983).

However, when pinacol rearrangement was conducted using

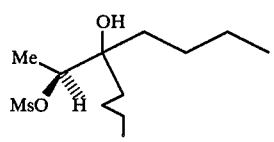

(wherein Me is a methyl group and Ms is a mesyl group) as a starting material and Et₃Al (Et is an ethyl group) as a reaction promoter, considerable amounts of epoxide

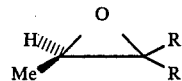

(wherein R indicates a hydrocarbon group having carbon atoms of 1 to 20) were produced secondarily.

There, using Et₂AlCl in place of Et₃Al, it was found that the reaction proceeded rapidly under mild conditions and yet without accompanying racemization, and the corresponding optically active ketone could be obtained in good yield.

Explaining the invention in detail, after Et₂AlCl (hexane solution, 2.5 equivalent weight) was added dropwise to a methylene chloride solution of active β-mesyloxy alcohol (I) at −78° C.,

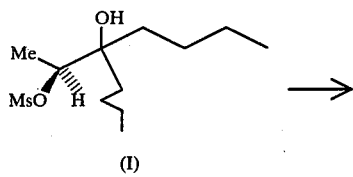

(I)

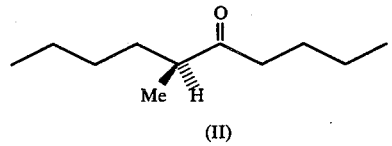

(II)

the mixture was stirred for 1 hour and the temperature was raised to 0° C. over 1 hour further. Treating this by an ordinary method, ketone (II) was obtained in a high yield of 90%.

When examined with regard to the optical purity of this ketone, it was pure optically. and it was recognized that this rearrangement reaction proceeded stereospecifically without accompanying racemization.

Moreover, the ability for the rearrangement in this reaction was much greater with aryl group and alkenyl group than with alkyl group, and it was recognized that Et₂AlCl was used successfully as a reaction promoter in the case of 1,2 rearrangement reaction with alkyl group which was low in the ability for the rearrangement.

This is conceivable due to that the formation of epoxide was suppressed as a result of the lowering of the nucleophilicity of alkoxide together with the stronger activation of mesyloxy group by using a promoter having a strong Lewis acidity.

Besides, though mesyl group was used in the preceding reaction, mesyl group and tosyl group can be put into effect similarly, and as the solvents, toluene, xylene, hexane, chlorobenzene, ether, etc. can be used in addition to methylene chloride.

In following, the invention is explained showing examples, but the invention is not confined to them.

Moreover, for reference, the synthesis of (S)-4-methyl-3-hexanone which is the alarm pheromone of the ant was shown as a referential example using (S)-ethyl lactate as a starting material and employing this reaction on the way.

EXAMPLE 1

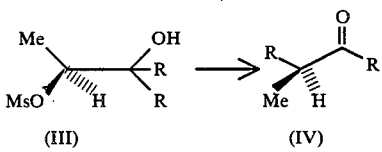

Following the above equation, after Et$_2$AlCl (hexane solution, 2.5 equivalent) was added dropwise to a methylene chloride solution of optically active β-mesyloxy alcohol at −78° C., the mixture was stirred for 1 hour and the temperature was raised to 0° C. over 1 hour further. Then, the mixture was treated at room temperature and observed the situation of 1,2 rearrangement by varying R in many ways.

The results are as shown in Table 1.

TABLE 1

| | Alcohol | R | Yield (%) | ee (%) (c) |
|---|---|---|---|---|
| (1) | (III) | n-Butyl | 90 | >95 (a) |
| (2) | (III) | n-Octyl | 90 | >95 (a) |
| (3) | (III) | Ethyl | 64 | >95 (a) |
| (4) | (III) | Cyclohexyl | 92 | >99 (b) |

(a) Determined with $^{13}$C NMR after forming the MTPA derivative (α-methoxy-α-phenylacetic acid) ester.
(b) Determined with forming HPLC after the derivatives MTPA ester.
(c) Enantiomeric excess.

The reaction proceeded in high yield and moreover stereospecifically in each case to give the objective optical active ketone (IV).

EXAMPLE 2

Synthesis of (S)-6-methyl-5-decanone

After 0.78 ml (0.78 mmol) of diethylaluminum chloride (hexane 1M solution) were added to a dried methylene chloride (3 ml) solution of 81.8 mg (0.31 mmol) of (S)-3-butyl-2-methanesulfonyloxy-3-heptanol (urefined) at −78° C. under stirring, and stirred for two and a half hours at −78° C., the temperature was raised to 0° C. over an hour and a half. The reaction was stopped with three drops of phosphoric acid buffer solution (pH 7). The resultant suspension was diluted with ethyl acetate, dried with anhydrous sodium sulfate, filtered and concentrated. The oily residue was separated and refined by the use of silica gel column chromatography (hexane/ethyl acetate=35/1) to obtain (S)-6-methyl-5-decanone as a pale yellow oily substance (46.9 mg, yield 90%).

IR (Film): 2970, 2950, 2880, 1720, 1460, 1380 cm$^{-1}$.
NMR (CCl$_4$): δ 0.8–1.8 (m, 10H), 0.9–1.1 (m, 9H), 2.2–2.6 (m, 3H)

EXAMPLE 3

Synthesis of (S)-6-methyl-5-decanone

After 0.95 ml (0.95 mmol) of ethylaluminum dichloride (hexane 1M solution) were added to a dried methylene chloride (3 ml) solution of 101.5 mg (0.38 mmol) of (S)-3-butyl-2-methanesulfonyloxy-3-heptanol (unrefined) at −78° C. under stirring, and stirred for two and a half hours at −78° C., the temperature was raised to 0° C. over an hour and a half. The reaction was stopped with three drops of phosphoric acid buffer solution (pH 7). The resultant suspension was diluted with ethyl acetate, dried with anhydrous sodium sulfate, filtered and concentrated. The oily residue was separated and refined by the use of silica gel column chromatography (hexane/ethyl acetate=35/1) to obtain (S)-6-methyl-5-decanone as a pale yellow oily substance (56.3 mg, yield 87%).

IR (Film): 2970, 2950, 2880, 1720, 1460, 1380 cm$^{-1}$.
NMR (CCl$_4$): δ 0.8–1.8 (m, 10H), 0.9–1.1 (m, 9H), 2.2–2.6 (m, 3H).

EXAMPLE 4

Experiment was carried out using ethylaluminum sesquichloride as a reaction promoter in place of Et$_2$AlCl under the same conditions as in Example 3. The result was approximately same as in the case of Et$_2$AlCl.

EXAMPLE 5

Synthesis of (S)-10-methyl-9-octadecanone

After 0.63 ml (0.63 mmol) of diethylaluminum chloride (hexane 1M solution) were added to a dried methylene chloride (3 ml) solution of 89.7 mg (0.24 mmol) of (S)-2-methanesulfonyloxy-3-octyl-3-undecanol (unrefined) at −78° C. under stirring, and stirred for two and a half hours at −78° C., the temperature was raised to 0° C. over an hour and a half. The reaction was stopped with three drops of phosphoric acid buffer solution (pH 7). The resultant suspension was diluted with ethyl acetate, dried with anhydrous sodium sulfate, filtered and concentrated. The oily residue was separated and refined by the use of silica gel column chromatography (hexane/ethyl acetate=35/1) to obtain (S)-10-methyl-9-octadecanone as a colorless oily substance (60.5 mg, yield 90%).

IR (Film): 2960, 2940, 2860, 1720, 1460, 1380 cm$^{-1}$.
NMR (CCl$_4$): δ 0.7–1.8 (m, 26H), 0.8–1.1 (m, 9H), 2.2–2.6 (m, 3H).

EXAMPLE 6

Synthesis of (S)-1,2-dicyclohexyl-1-propanone

After 1.0 ml (1.0 mmol) of diethylaluminum chloride (hexane 1M solution) were added to a dried methylene chloride (3 ml) solution of 130.5 mg (0.41 mmol) of (S)-2-methanesulfonyloxy-1,1-dicyclohexyl-1-propanol (unrefined) at −78° C. under stirring, and stirred for two and a half hours at −78° C., the temperature was raised to 0° C. over an hour and a half. The reaction was stopped with three drops of phosphoric acid buffer solution (pH 7). The resultant suspension was diluted with ethyl acetate, dried with anhydrous sodium sulfate, filtered and concentrated. The oily residue was separated and refined by the use of silica gel column chromatography (hexane/ethyl acetate=35/1) to obtain (S)-1,2-dicyclohexyl-1-propanone as a pale yellow oily substance (84.1 mg, yield 92%).

IR (Film): 2950, 2860, 1710, 1450, 1380, 1140, 990, 890 cm$^{-1}$.

NMR (CCl$_4$): δ 0.7-1.9 (m, 21H), 0.9 (d, J=7 Hz, 3H), 2.1-2.5 (m, 2H).

REFERENTIAL EXAMPLE

(1) Synthesis of (S)-3-ethyl-2,3-pentanediol (S)-ethyl lactate (6.56 g, 55.5 mmol) was dissolved into dried tetrahydrofuran (35 ml). After ethylmagnesium bromide (1.33M tetrahydrofuran solution, 150 ml) was added to this under cooling with ice, and stirred for 4 hours at room temperature, the reaction was stopped by adding phosphoric acid buffer solution (pH 7).

The product was extracted with ethyl acetate, and the extracted liquid was concentrated under vacuum after dried with anhydrous magnesium sulfate. When the oily residue thus obtained was separated and refined by the use of silica gel flash column chromatography (hexane/ethyl acetate=1.5/1, (S)-3-ethyl-2,3-pentanediol was obtained as a pale yellow oily substance (6.22 g, 85%).

NMR (CDCl$_3$): δ 0.8-1.2 (m, 9H), 1.3-1.8 (m, 4H), 2.0-2.5 (m, 2H), 3.7 (q, J=6 Hz, 1H).

(2) Synthesis of (S)-3-ethyl-2-methanesulfonyloxy-3-pentanol

After a dried methylene chloride (5 ml) solution of 4.04 g (40.0 mmol) of triethylamine was added to a dried methylene chloride (20 ml) solution of 2.64 g (19.9 mmol) of (S)-3-ethyl-2,3-pentanediol, a dried methylene chloride (5 ml) solution of 3.43 g (30.0 mmol) of methanesulfonyl chloride was further added to this under cooling with ice, and stirred for 1 hour at 0° C., the reaction was stopped by adding phosphoric acid buffer solution (pH 7).

The water layer was extracted with ethyl acetate (15 ml×3 times), and the extracted liquid was washed in sequence with saturated aqueous solution of oxalic acid (15 ml×2 times), saturated common salt solution (15 ml×1 time), 4% sodium bicarbonate solution (15 ml×2 times) and saturated common salt solution (15 ml×1 time). After dried with anhydrous sodium sulfate, the liquid was concentrated under vacuum to obtain 4.14 g of (S)-3-ethyl-2-methanesulfonyloxy-3-pentanol as a yellow oily substance.

Yield 99% (unrefined).

(3) Synthesis of (S)-4-methyl-3-hexanone

After 50 ml (50 mmol) of diethylaluminum chloride (hexane 1M solution) were added to a dried methylene chloride (15 ml) solution of 4.14 mg (19.7 mmol) of (S)-3-ethyl-2-methanesulfonyloxy-3-pentanol (unrefined) at −78° C. under stirring, and stirred for two and a half hours at −78° C., the temperature was raised to 0° C. over an hour and a half. After the reaction liquid was poured into a cooled saturated aqueous solution of ammonium chloride, water was added, and the product was extracted with diethyl ether (10 ml×4 times).

The extracted liquid was washed with saturated common salt solution, and then, dried with anhydrous magnesium sulfate. After the extracted liquid was distilled under atmospheric pressure to remove the solvent alone, the residue obtained was submitted to the vacuum distillation (oven temperature 85°-95° C./200 mm Hg) with Kugelrohr (bulb tube) to obtain (S)-4-methyl-3-hexanone as a colorless oily substance (1.45 g, 64%).

IR (CHCl$_3$ in KBr solution cell): 2970, 2950, 2890, 1710, 1460, 1380 cm$^{-1}$.

NMR (CDCl$_3$): δ 0.8-1.1 (m, 9H), 1.0-1.9 (m, 2H), 2.3-2.6 (m, 3H).

What is claimed is:

1. In a Pinacol-type rearrangement, the improvement comprising:

contacting an optically active sulfonyloxy alcohol of the formula:

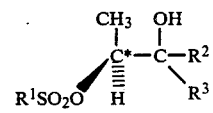

wherein R$^1$, R$^2$ and R$^3$ are each independently a C$_1$ to C$_{20}$ hydrocarbon group which may contain N, O, P or S, and * indicates an asymmetric carbon atom, with an organoaluminum compound of the formula R$^4{}_{3-n}$AlX$_n$ wherein R$^4$ is a C$_1$ to C$_{20}$ alkyl group, X is a halogen atom, an alkoxy group or a CN group, and n is 1, 1.5 or 2, to obtain an optically active ketone of the formula:

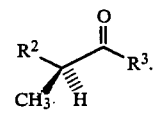

2. The Pinacol-type rearrangement of claim 1, wherein the said organoaluminum compound comprises diethylaluminum chloride, ethylaluminum dichloride or ethylaluminum sesquichloride.

3. The Pinacol-type rearrangement of claim 1, wherein the said rearrangement is conducted of a temperature from room temperature to −80° C.

4. The Pinacol-type rearrangement of claim 1, wherein the said rearrangement is run in a solvent comprising methylene chloride, toluene, xylene, hexane, chlorobenzene or ether.

5. The Pinacol-type rearrangement of claim 1, wherein the said organoaluminum compound is diethylaluminum chloride.

6. The Pinacol-type rearrangement of claim 1, wherein the said organoaluminum compound is ethylaluminum dichloride.

7. The Pinacol-type rearrangement of claim 1, wherein the said organoaluminum compound is ethylaluminum sesquichloride.

* * * * *

UNITED STATES PATENT AND TRADEMARK OFFICE
CERTIFICATE OF CORRECTION

PATENT NO. : 4,604,486

DATED : August 5, 1986

INVENTOR(S) : Tsuchihashi, Genichi et al

It is certified that error appears in the above-identified patent and that said Letters Patent is hereby corrected as shown below:

```
On the title page insert
-- (30) Foreign Application Priority Data
    March 1,1984      Japan        59-39464 --.
```

Signed and Sealed this

Fourteenth Day of October, 1986

[SEAL]

*Attest:*

DONALD J. QUIGG

*Attesting Officer*    *Commissioner of Patents and Trademarks*